United States Patent
Berndtsson (10) Patent No.: US 7,335,339 B2
(45) Date of Patent: Feb. 26, 2008

(54) DISPOSABLE APPARATUS FOR USE IN BLOOD TESTING

(75) Inventor: Ingemar Berndtsson, Sollentuna (SE)

(73) Assignee: Boule Medical AB, Stockholm (SE)

( * ) Notice: Subject to any disclaimer, the term of this patent is extended or adjusted under 35 U.S.C. 154(b) by 193 days.

(21) Appl. No.: 10/849,239

(22) Filed: May 20, 2004

(65) Prior Publication Data
US 2004/0213699 A1    Oct. 28, 2004

Related U.S. Application Data (63) Continuation of application No. PCT/SE02/02093, filed on Nov. 18, 2002.

(51) Int. Cl.
*B01L 3/00* (2006.01)
(52) U.S. Cl. ............ 422/102; 422/68.1; 422/73; 422/100; 436/69; 436/70; 436/174; 436/179; 436/180
(58) Field of Classification Search ............ 422/68.1, 422/73, 99, 100, 102; 436/62, 63, 66, 174–180, 436/69, 70
See application file for complete search history.

(56) References Cited

U.S. PATENT DOCUMENTS

| | | | | |
|---|---|---|---|---|
| 4,799,393 A | * | 1/1989 | Uffenheimer | 73/864.22 |
| 5,077,017 A | * | 12/1991 | Gorin et al. | 422/100 |
| 5,104,813 A | * | 4/1992 | Besemer et al. | 436/179 |
| 5,294,336 A | * | 3/1994 | Mizuno et al. | 210/198.2 |
| 5,316,730 A | * | 5/1994 | Blake et al. | 422/73 |
| 5,558,838 A | * | 9/1996 | Uffenheimer | 422/100 |
| 5,652,149 A | * | 7/1997 | Mileaf et al. | 436/518 |
| 6,016,712 A | * | 1/2000 | Warden et al. | 73/864.21 |
| 6,284,548 B1 | | 9/2001 | Berndtsson | |
| 6,387,328 B1 | * | 5/2002 | Berndtsson | 422/73 |

FOREIGN PATENT DOCUMENTS

| | | |
|---|---|---|
| WO | WO 95/18962 A1 | 7/1995 |
| WO | WO 98/22797 A1 | 5/1998 |
| WO | WO 99/01742 A1 | 1/1999 |
| WO | WO 01/75416 A1 | 10/2001 |

* cited by examiner

*Primary Examiner*—Jill Warden
*Assistant Examiner*—Dwayne K. Handy
(74) *Attorney, Agent, or Firm*—Birch, Stewart, Kolasch & Birch, LLP (57) ABSTRACT

A disposable apparatus for use in blood testing and being adapted for simultaneous dilution of a blood sample into two different dilution ratios, said apparatus including a block-shaped housing having integrated therein a first and a second receptacle, one of which as a first blood sample receiver being adapted to receive a blood sample; a first and a second container, each containing a defined volume of a diluent; a valve including a valve body having three valve body channels extending therethrough and being positionable in three distinct positions, one of which putting the receptacles in simultaneous communication with a respective one of the containers through pairs of the channels; and displacers for displacing diluent and diluted sample through said channels between said containers and said receptacles.

20 Claims, 12 Drawing Sheets

DISPOSABLE APPARATUS FOR USE IN BLOOD TESTING

This application is a Continuation of co-pending PCT International Application No. PCT/SE02/02093 filed on Nov. 18, 2002, which designated the United States, and on which priority is claimed under 35 U.S.C. § 120, and 35 U.S.C. § 119(a) on Patent Application No(s). 0103877-7 filed in Sweden on Nov. 21, 2001, the entire contents of which are hereby incorporated by reference.

The present invention concerns a disposable apparatus for use in blood testing.

When making blood tests in the field, it is a desire to perform such tests with simple but reliable apparatus that can be handled even by relatively untrained personnel. Still, there exists the requirement that a blood sample shall be taken and handled under strict hygienic conditions, and that neither the sample itself or residues thereof, nor diluting or flushing liquids used when testing the sample shall risk to be contacted by humans. Thus, there shall be no waste matter and all contaminated material shall remain within the apparatus.

It is known in the state of art to count blood cells by causing a volume of diluted blood sample to pass a so-called capillary, i.e., an extremely small hole, generally in a ruby, the hole having a diameter considerably larger than the size of a blood cell, typically 80 µm. A voltage is applied over the capillary, and, when a blood cell passes through the hole, the electrical resistance changes. This is because the cells can be regarded as insulators. Each change in resistance can be detected by suitable electronic equipment, and the sum of all changes detected corresponds to the number of blood cells having passed through the capillary. In order to obtain the concentration of cells in the original sample, the concentration of cells in the diluted sample is multiplied by the dilution factor, typically 1:40000 when counting of red blood cells (RBC) is concerned. It is obvious, that measuring of sample volumes and dilution liquid volumes must be performed in an accurate and repeatable way such that not only a correct degree of dilution can always be guaranteed but also a thorough and uniform mixing of the two volumes is ensured.

A disposable sampling device for an apparatus for counting particles contained in a liquid, such as blood cells in a blood sample, is known from WO 99/01742. This device is capable of making one diluting step.

A blood testing apparatus for performing dilution of a small defined volume of blood sample contained in a capillary tube is described in U.S. Pat. No. 6,284,548. The dilution involves a pre-dilution step and a final dilution step.

A device for diluting and mixing a liquid sample, such as a blood sample for performing a CRP test, is described in WO 01/75416. The sample is contained in a capillary tube and is mixed in a first step with a diluting agent to provide a diluted sample. In a second step, a third medium, such as antibodies, may be mixed with the diluted sample.

Even if some of the prior art devices are capable of making two dilutions, none of them is capable of making two simultaneous dilutions to different dilution ratios, which is desirable in order to perform, e.g., simultaneous counting of white and red blood cells.

It is a main object of the present invention, thus, to provide a disposable apparatus for use in blood testing, which allows simultaneous dilution of a blood sample to two defined dilutions ratios. Also, in order to avoid waste, the disposable apparatus shall be capable of retaining all contaminated material within itself. It is also an object of the present invention to propose an instrument for use with the apparatus.

To fulfill the main object above, the present invention proposes a disposable apparatus for use in blood testing and being adapted for simultaneous dilution of a blood sample into two different dilution ratios, said apparatus including a block-shaped housing having integrated therein: a first and a second receptacle, one of which, as a first blood sample receiver, being adapted to receive a blood sample; a first and a second container, each containing a defined volume of a diluent; a valve including a valve body having three valve body channels extending therethrough and being positionable in three distinct positions, one of which bringing the receptacles in simultaneous communication with a respective one of the containers through pairs of the channels; and displacers for displacing diluent and diluted sample through said channels between said containers and said receptacles. The displacers may be pistons movable in cylinders provided in the housing, or, an external source of pressure may be utilized to displace diluent and diluted sample.

The invention will now be described in connection with an embodiment thereof utilizing a turning valve, and pistons as displacers, reference being made to the accompanying schematic drawings, wherein.

It is evident for the skilled person that the present invention may as well be practiced utilizing a sliding valve instead of the turning valve specifically described.

I the following description, the terms upper, lower, right, left etc., refer to the position of the apparatus shown in the various Figures.

The overall structure of the apparatus will first be described with reference to FIG. 1. It consists of a block-like housing 1 (see also the side view of FIG. 9) preferably made of a translucent, moldable material. The housing has an upper end 2, a bottom end 3, a left side wall 4, a right side wall 5, a front wall 6 and a rear wall 7 seen in FIG. 9 only.

In a central portion of the housing is provided a cylindrical hole 8. Two channels 9 and 10 extending towards the upper end 2 open in the hole 8 at spaced locations along its upper circumference. Correspondingly, two channels 11 and 12 extending towards the bottom end 3 open in the hole 8 at spaced locations along its lower circumference.

A turning valve body 13 dimensioned to fit into the hole 8 is placed therein so as to be rotatable between at least three distinct positions. Three separate channels, a first channel 14, a second channel 15 and a third channel 16, extend through the valve body between mutually diametrically opposed positions along the circumference of the valve body. The channels are angularly spaced such that there is a substantially 60° angular distance between them along the circumference. By turning the valve body, the channels 14-16 may be positioned so as to cross-wise put the channels 9/12 and 10/11 in communication with one another.

Figure 1:
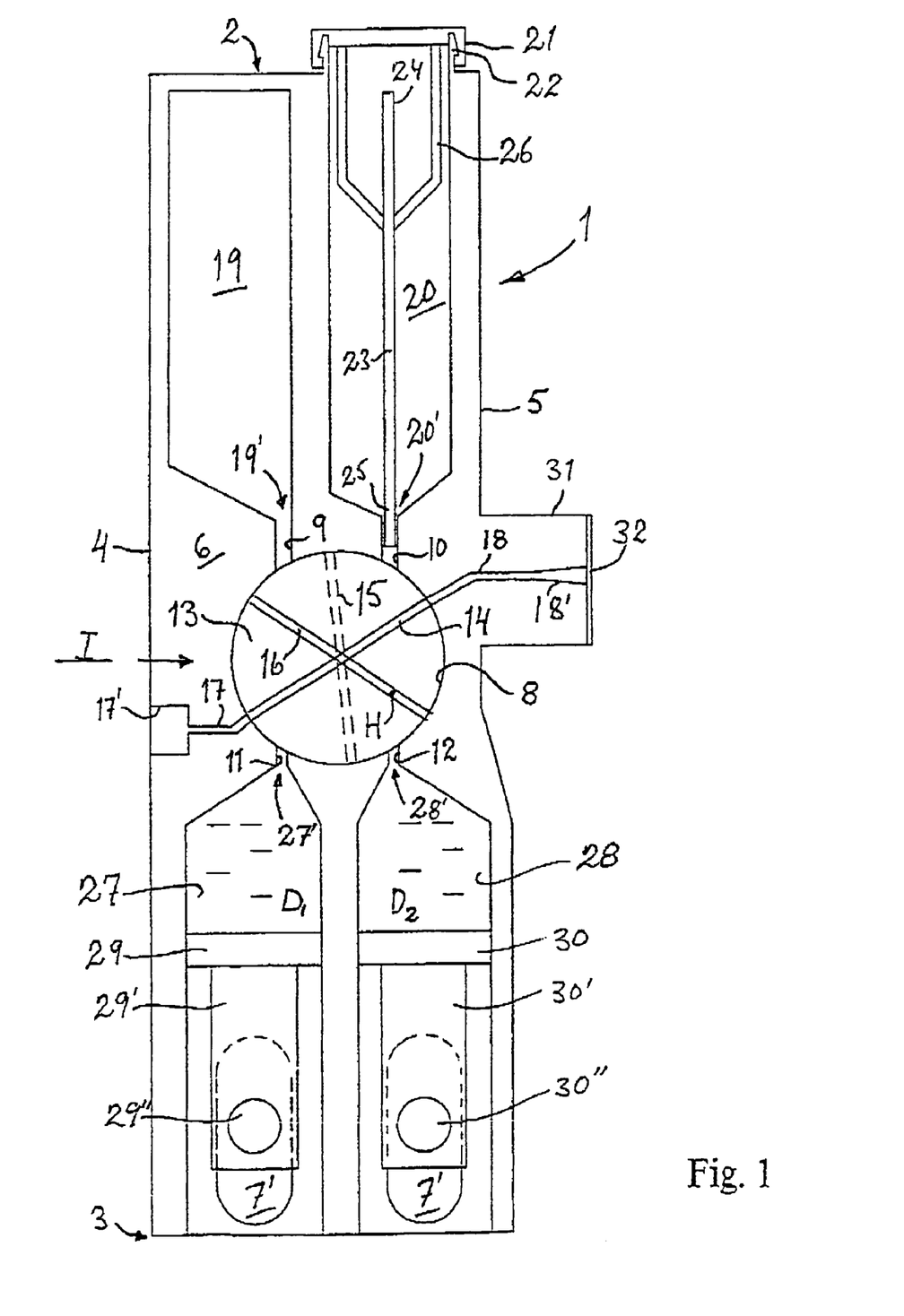
FIG. 1 is a front view showing the apparatus in its preparatory state including a capillary tube held by a cover.

The valve body is shown in FIG. 1 in a first rotational position I. In this position, the preparatory position, none of the channels 14-16 communicate with the channels 9/12 and 10/11. It can be seen however, that one end of the channel 14 communicates with a channel 17 extending between a position along the left portion of the circumference of the hole 8 and the left side wall 4, and that its opposite end communicates with a channel 18 extending between an opposed portion along the right portion of the circumference of the hole 8. The purpose of this communication will be explained later with reference to FIGS. 6 and 7.

In the upper portion of the housing 1 are formed two receptacles 19, 20, preferably formed like parallel bores. A first one of these, receptacle 19, has its lower end 19' connected to the channel 9. Its upper end is shown to be closed, but it may as well be open and closed by any suitable removable cover. A second one of the receptacles, receptacle 20, has its lower end 20' connected to the channel 10. Its upper end is closed by a preferably circular cover 21 snapped into engagement with a hook-like protrusion 22 formed at the upper end 2 of the housing.

The cover 21 is shown to carry a capillary tube 23 having an upper end 24 and a lower end 25. The tube is mounted in the cover by means of ribs 26 depending from the cover such that the upper end of the tube opens in an open space between the ribs communication with atmosphere.

As an alternative option, there may be provided a separate cover 21 to close the receptacle 20 and a separate combination of a cover 21 and a capillary tube as shown.

In the lower portion of the housing 1 are formed two parallel cylinders 27, 28. A first one of these, cylinder 27, has its upper end 27' connected to the channel 11. A second of the cylinders 28 has its upper end 28' connected to the channel 12. A first piston 29 is slidably reciprocatingly movable along the cylinder 27. A second piston 30 is slidably reciprocatingly movable along the cylinder 28. The pistons have piston rods 29', 30', respectively, each having in a lower end thereof a through hole 29'', 30'', respectively.

The holes 29'', 30'' are accessible through vertically extending apertures 7' in the rear wall 7 of the housing.

The right hand wall 5 of the housing is provided with a cylindrical protrusion 31, in the centre of which opens the channel 18 with a slightly widening mouth portion 18'. An elastic diaphragm 32 seals the mouth portion 18'.

In the preparatory state of the apparatus, the cylinders 27 and 28 are both filled with well-defined volumes, typically 2 ml, of diluting agent $D_1$, $D_2$, respectively, typically isotonic sodium chloride solution. Furthermore, the channel 16 is filled with an appropriate amount of a haemolysis agent H, which may be in a dried or a fluid state. In the first position I of the valve body 13, where the ends of the channel 16 are located at a distance from any one of the housing channels 9, 12, 17, 18, the haemolysis agent H is effectively prevented from escaping the channel 16.

Figure 2:
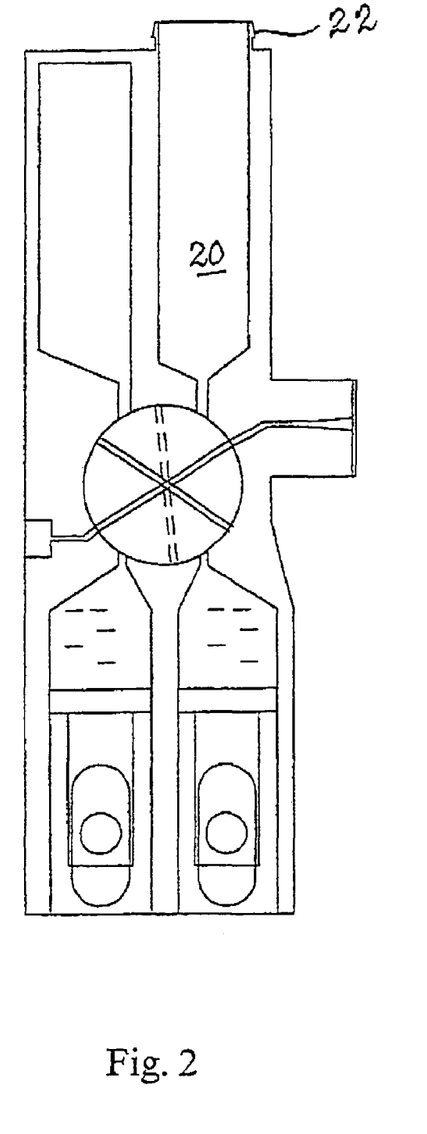
FIG. 2 is a corresponding view showing the apparatus with its capillary tube and cover removed.
Figure 3:
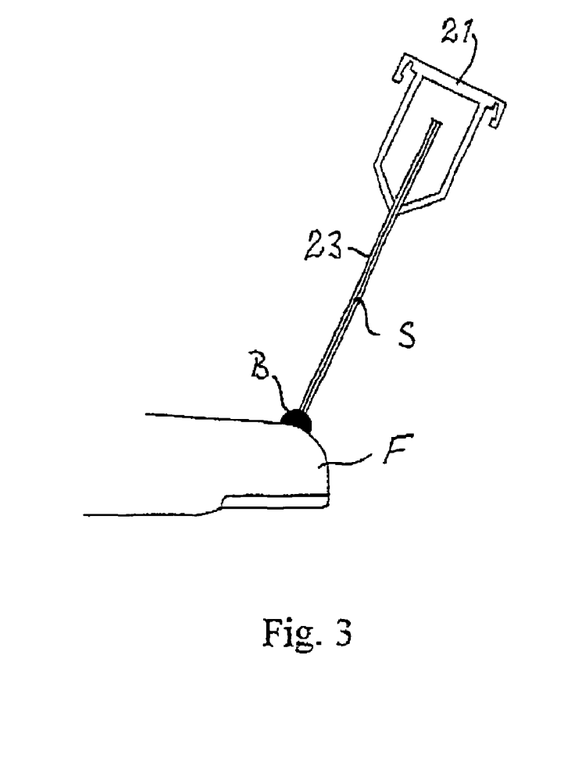
FIG. 3 is a view showing the removed capillary tube in a position receiving a blood sample from punctured finger tip.
Figure 4:
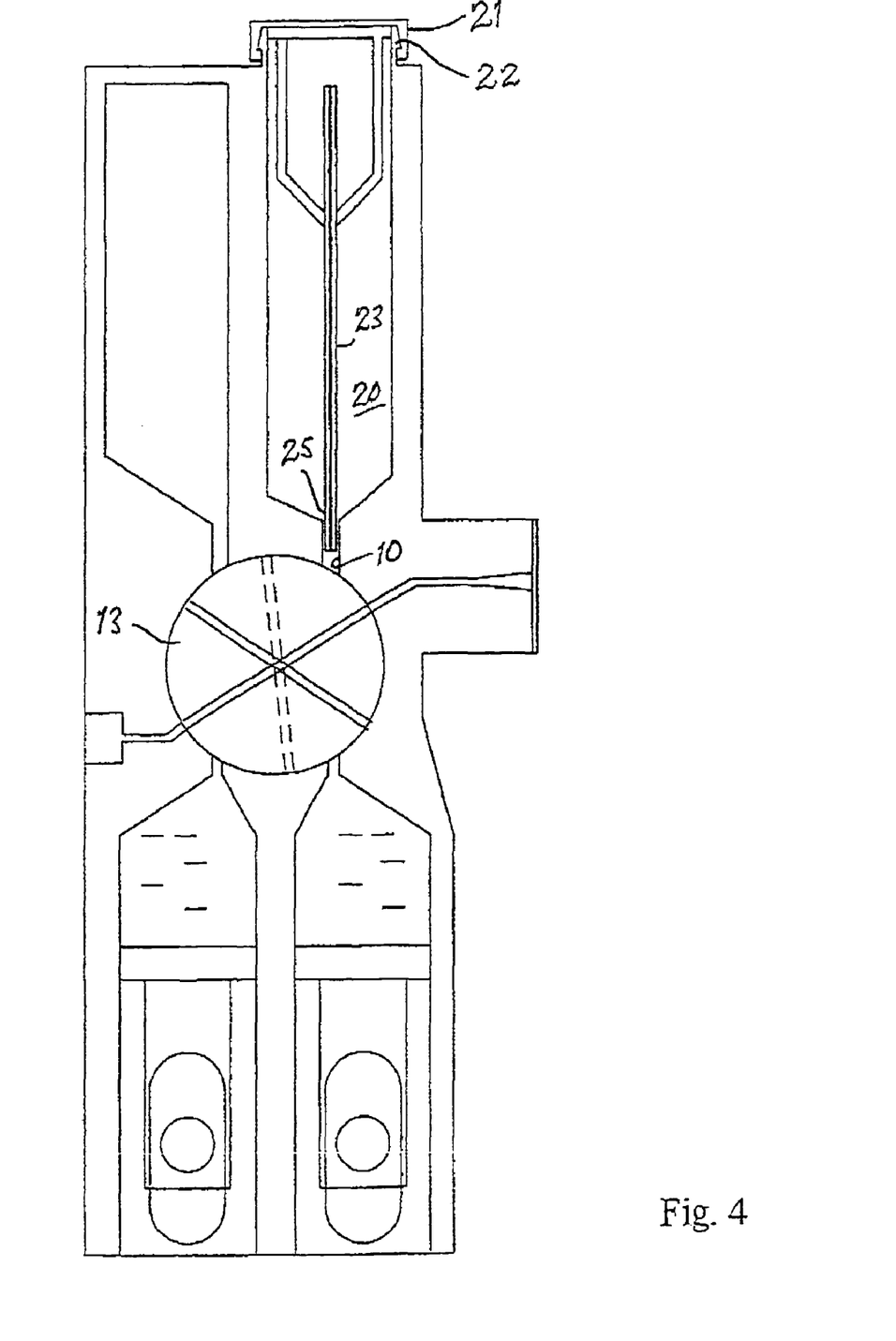
FIG. 4 is a view corresponding that of FIG. 2 showing the apparatus with the capillary tube and its blood sample relocated in its original position within the apparatus.

In a first mode of operation shown in FIGS. 2 and 3, the apparatus is used in finger tip blood sampling. The cover 21—and with it the capillary tube 23—is removed from the housing 1, and a blood sample S is taken with the capillary tube as illustrated in FIG. 3. The tube is approached to a drop of blood B formed on a punctured finger tip F, and the drop is sucked up by capillary action to completely fill the tube with a defined volume of sample S. During this operation, the cover 21 serves as a handle, thus avoiding any contact with the sample. After the sample is taken, the capillary tube is re-inserted into the receptacle 20 as seen in FIG. 4, and the cover 21 is pushed down to snap into sealing contact with the protrusions 22. In this position, the lower end 25 of the capillary tube may be more (as shown) or less introduced into the channel 10.

Figure 5:
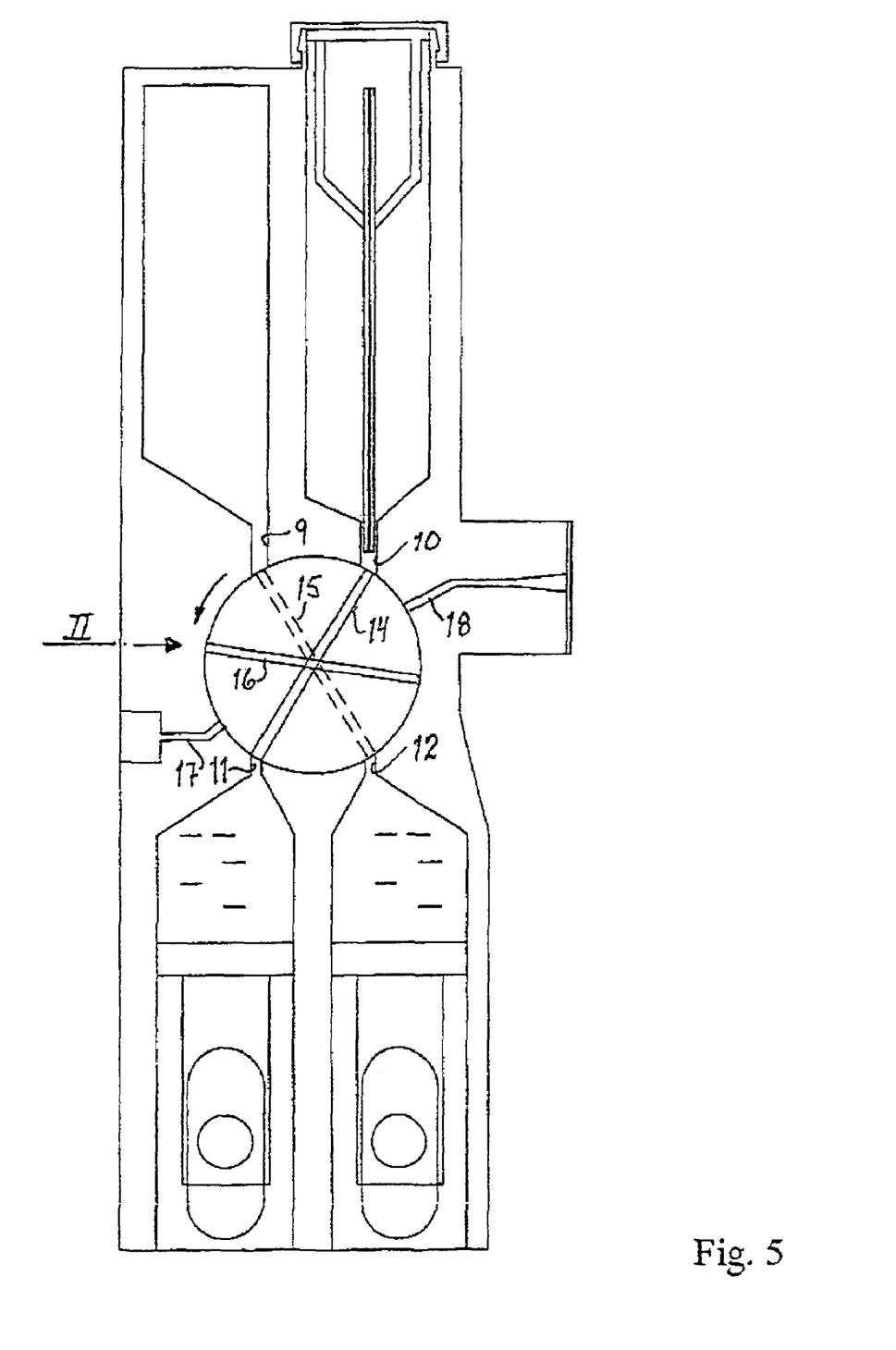
FIG. 5 is a front view of the apparatus as shown in FIG. 4 having the turning valve rotated one step to a second position.

In the state according to FIG. 4, the turning valve 13 is rotated one step counterclockwise to the second rotational position II shown in FIG. 5, where the housing channels 9 and 12 communicate through valve channel 15 and the housing channels 10 and 11 communicate through valve channel 14. In practice, the housing is placed in an associated instrument, as will be described later, for automatic performance of the valve rotation.

Figure 6A:
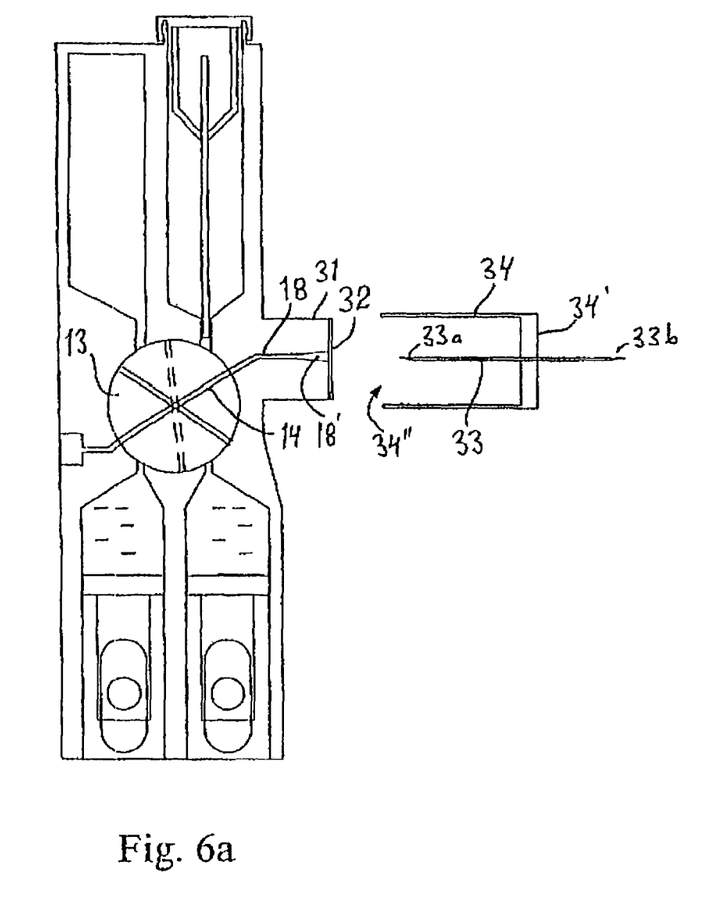
FIGS. 6a and b are front views showing the apparatus in its preparatory state according to FIG. 1 and illustrating a further possibility to charge the apparatus with a blood sample.
Figure 6B:
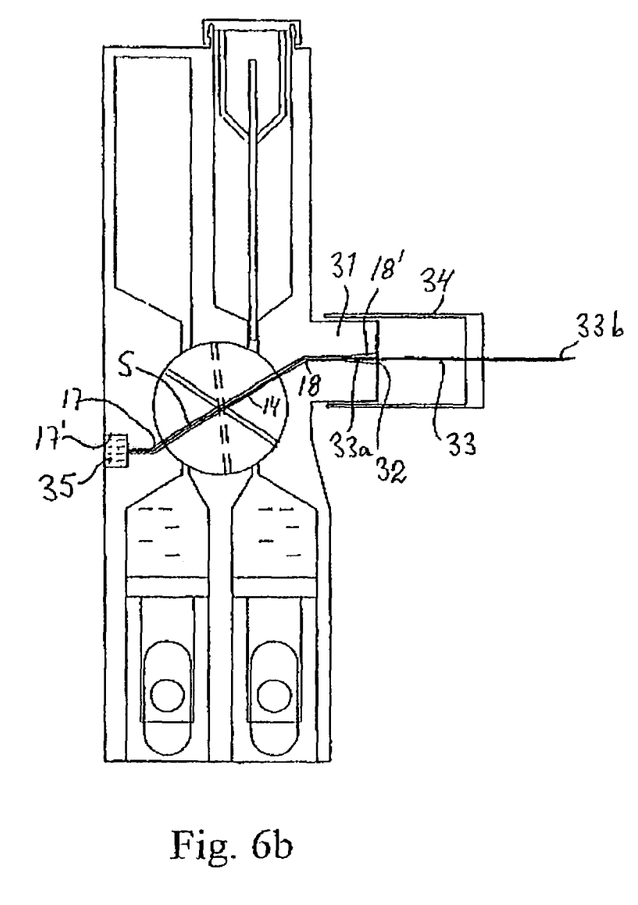

In a second mode of operation shown in FIGS. 6a and 6b, the apparatus is used in venipuncture sampling. When taking a venipuncture sample, blood is introduced into the channel 18 to pass into and through the valve body channel 14. This is suitable made by an injection needle or cannula 33 by which the diaphragm is pierced. Preferably, a so-called vacuutainer sleeve 34 is used, i.e., a device commonly used in connection with a so-called vacuutainer. A vacuutainer sleeve is a cylindrical hollow body having a bottom 34' centrally carrying the needle 33, and having an open end 34''. The needle has both its end chamfered so as to provide sharpened points 33a, 33b. The exterior dimension of the protrusion 31 is adapted to the interior dimension of the open end 34'' of the vacuutainer sleeve, so that the latter may be pushed onto the protrusion 31 with the needle point 33a penetrating the diaphragm 32 and being introduced into the channel mouth 18'. In this position, the housing 1 with the vacuutainer sleeve may be manipulated so as to bring the needle point 33b to puncture a vein. The venous pressure will force blood through the needle 33, the channel 18, the channel 14 into the channel 17 as seen in FIG. 6b, where a sample S is shown to occupy the interiors of the needle 33 and the channels 18, 14 and 17. A widened portion 17' of the channel 17 is suitably provided with a plug 35 of a material, such as a textile material, having the properties to allow air, but preventing blood flow therethrough. After the sample is taken, the needle point 33b is withdrawn from the punctured vein and, subsequently, the needle point 33a is withdrawn from the channel mouth 18' and from the pierced diaphragm 32. Due to the elasticity of the latter, it will seal itself and prevent any escape of blood from the portion of the sample within the channel 18.

Figure 7:
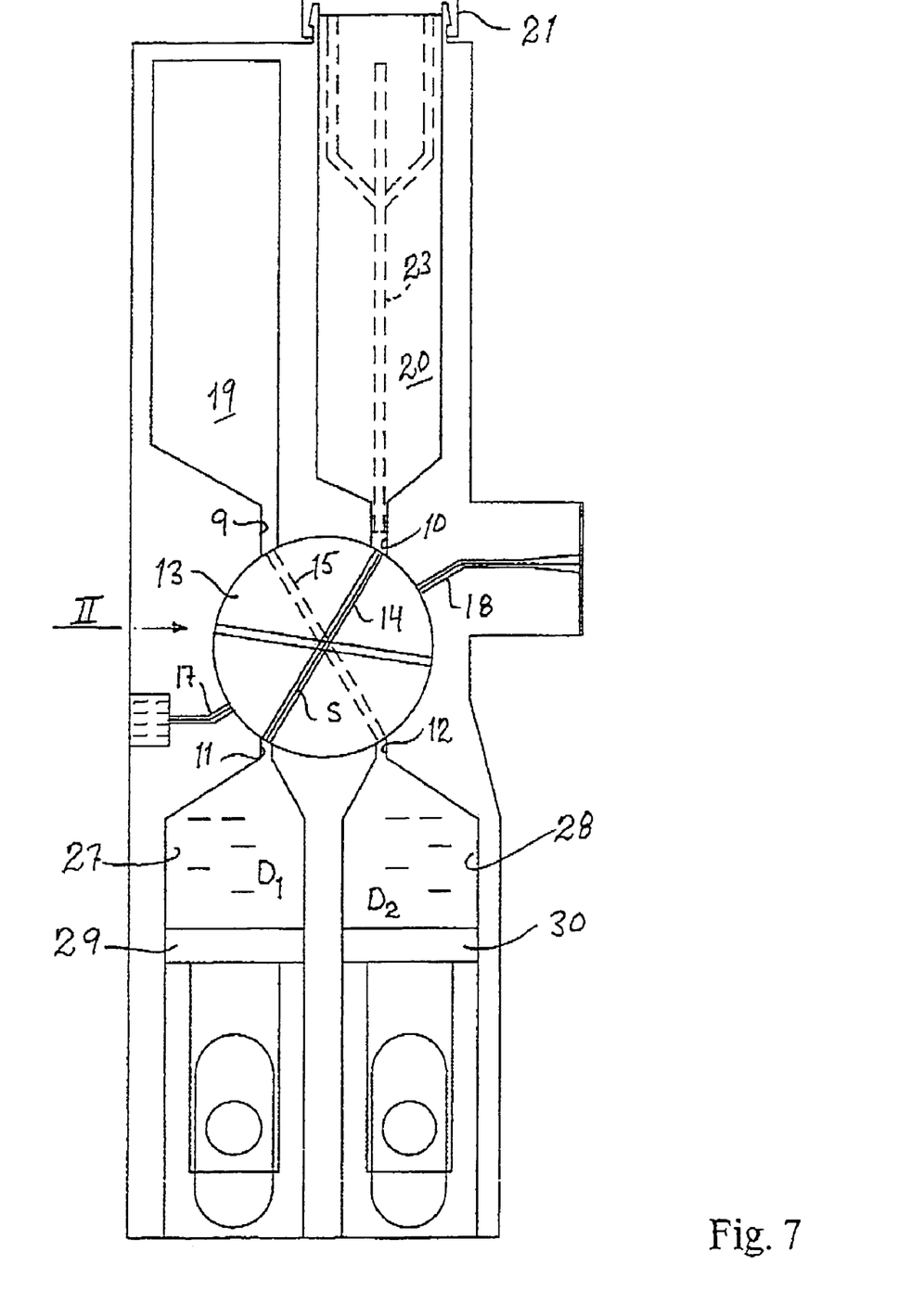
FIG. 7 is a view corresponding to that of FIG. 6b showing the apparatus with the turning valve rotated one step to a second position.

In the state according to FIG. 6*b*, the turning valve 13 is rotated one step counterclockwise to the second rotational position II shown in FIG. 7, thereby separating the defined volume of blood sample S contained within the channel 14 from the volumes contained within the housing channels 17 and 18, and further placing the housing channels 9 and 12 in mutual communication through the valve body channel 15 and the housing channels 10 and 11 in mutual communication through the valve body channel 14. In practice, the housing is placed in an associated instrument, as will be described later, for automatic performance of the valve rotation.

It is noted in FIG. 7, that the capillary tube 23 is shown in dotted lines to indicate its option in this mode, whereas the cover 21 is shown in full lines.

It is furthermore noted, that the rotational positions II of the valve body 13 shown in FIGS. 5 and 7 are the very same, and that the only difference is that the blood sample S is within the capillary tube 23 in FIG. 5 and within the valve body channel 14 in FIG. 7. In this position, common to both modes of operation, both pistons 29 and 30 are operated in a positive (i.e., upward) direction so as to displace the defined volume of diluent agent $D_1$ from the cylinder 27 through the channels 11, 14 and 10 into the receptacle 20, and so as to displace the defined volume of diluent $D_2$ from the cylinder 28 through the channels 12, 15 and 9 into the receptacle 19.

Figures 8, 9:
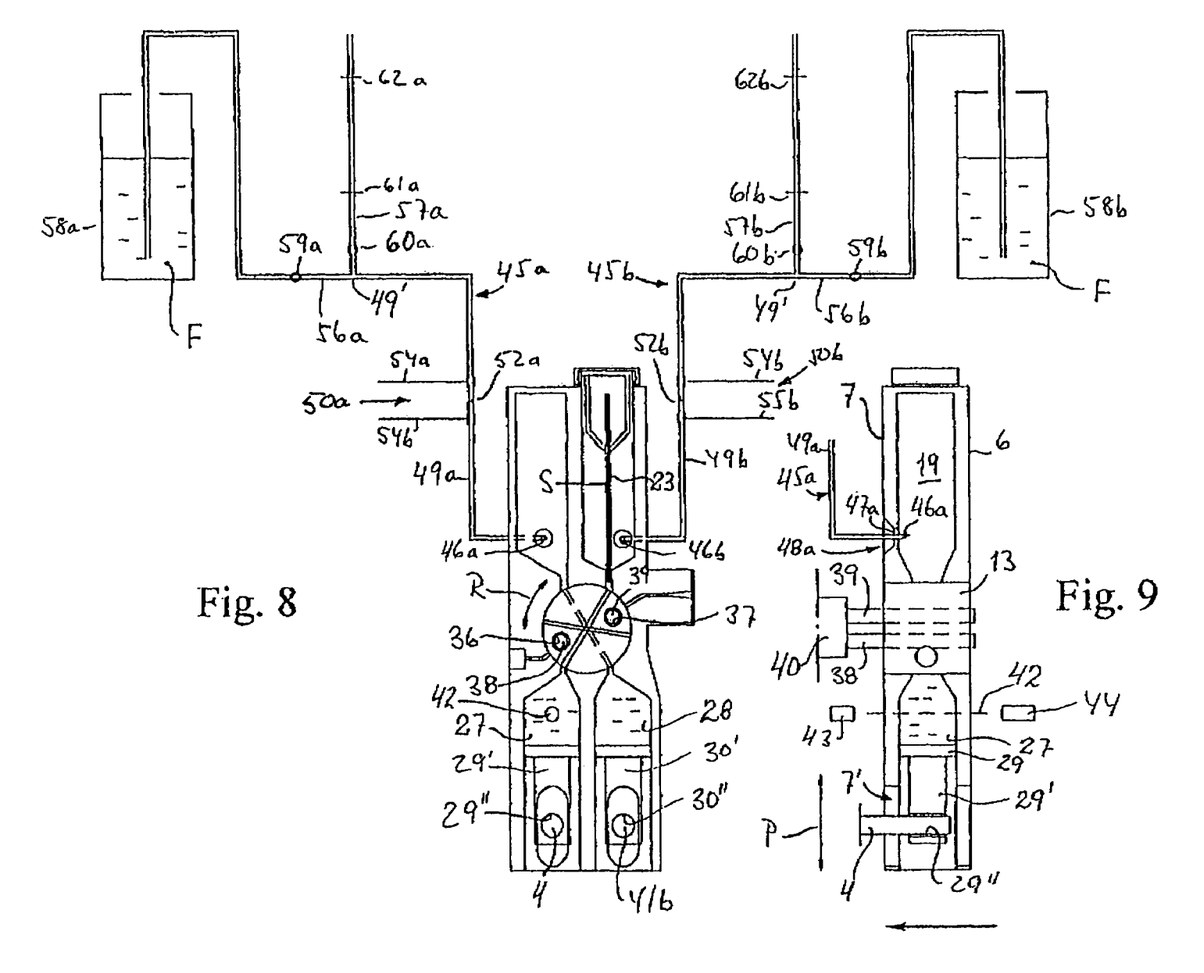
FIG. 8 is a front view of the apparatus as shown in FIGS. 5 and 7 connected to schematically shown external fluid conduits and valve and plunge actuating means of a test instrument.
FIG. 9 is a side view of the apparatus as shown in FIG. 8 and parts of the test instrument.

Turning now to FIGS. 8 and 9, these figures show the apparatus housing 1 placed in an instrument having means for rotating the turning valve body 13 and for operating the pistons 29, 30, as well as means for performing certain measurements.

As shown in FIG. 8, the valve body 13 is provided with two diametrically opposed holes 36, 37. When the apparatus housing is placed in the instrument, two operating arms 38, 39 of a rotatable valve operating member 40 engage in a respective one of these holes as seen in the side view of FIG. 9. Simultaneously, two piston operating arms 41*a*, 41*b* engage in a respective one of the through holes 29''', 30'' in the piston rods 29', 30'. The valve operating member 40 is rotatable in the directions of the double arrow R in FIG. 8, and the piston operating arms 40, 41 are vertically movable so as to move the pistons in the directions of the double arrow P in FIG. 9. Such movement is preferably simultaneous for both pistons.

FIG. 8 shows a situation corresponding to that of FIG. 5, i.e., with the blood sample S within the capillary tube 23. An upward stroke of the piston 29 will direct the diluent $D_1$ through the channel 10 (see FIG. 10) and at least partly through the capillary tube 23 having its lower end 25 introduced therein. Consequently, the sample S will be displaced upwardly from the capillary tube and flow from its upper end 24 down into the receptacle 20, where it will mix with parts of the diluent having passed through the annular space 10' formed between the lower end 25 of the capillary tube and the channel 10. A subsequent downward stroke of the piston 29 will withdraw the mixture (S+$D_1$) of sample S and diluent $D_1$ from the receptacle 20 through the annular space 10' to flow into the cylinder 27. Further subsequent strokes according to the arrow P will complete this mixing operation, which is a first stage mixing operation. Simultaneous strokes of the piston 30 in the directions P will only force the diluent $D_2$ from the cylinder 28 into the receptacle 19 and back.

In the second mode of operation, an upward stroke of piston 29 will displace the diluent $D_1$ through the channel 14 and consequently bring along the defined volume of sample S contained within the channel 14 directly into the recipient 20 in case there is no capillary tube 23 present, and partly through such tube if one is present. Subsequent strokes according to arrow P will complete the first stage mixing operation as in the first mode of operation.

In FIG. 8 is shown a circle indicating a light path 42 through the cylinder 27. This light path is also shown in FIG. 9 to extend between a light source 43 and a detector 44. The light path may be used to measure firstly a reference value of the diluent $D_1$ and subsequently a value after the first stage diluting step, i.e., of the diluted sample (S+$D_1$).

Figure 10:
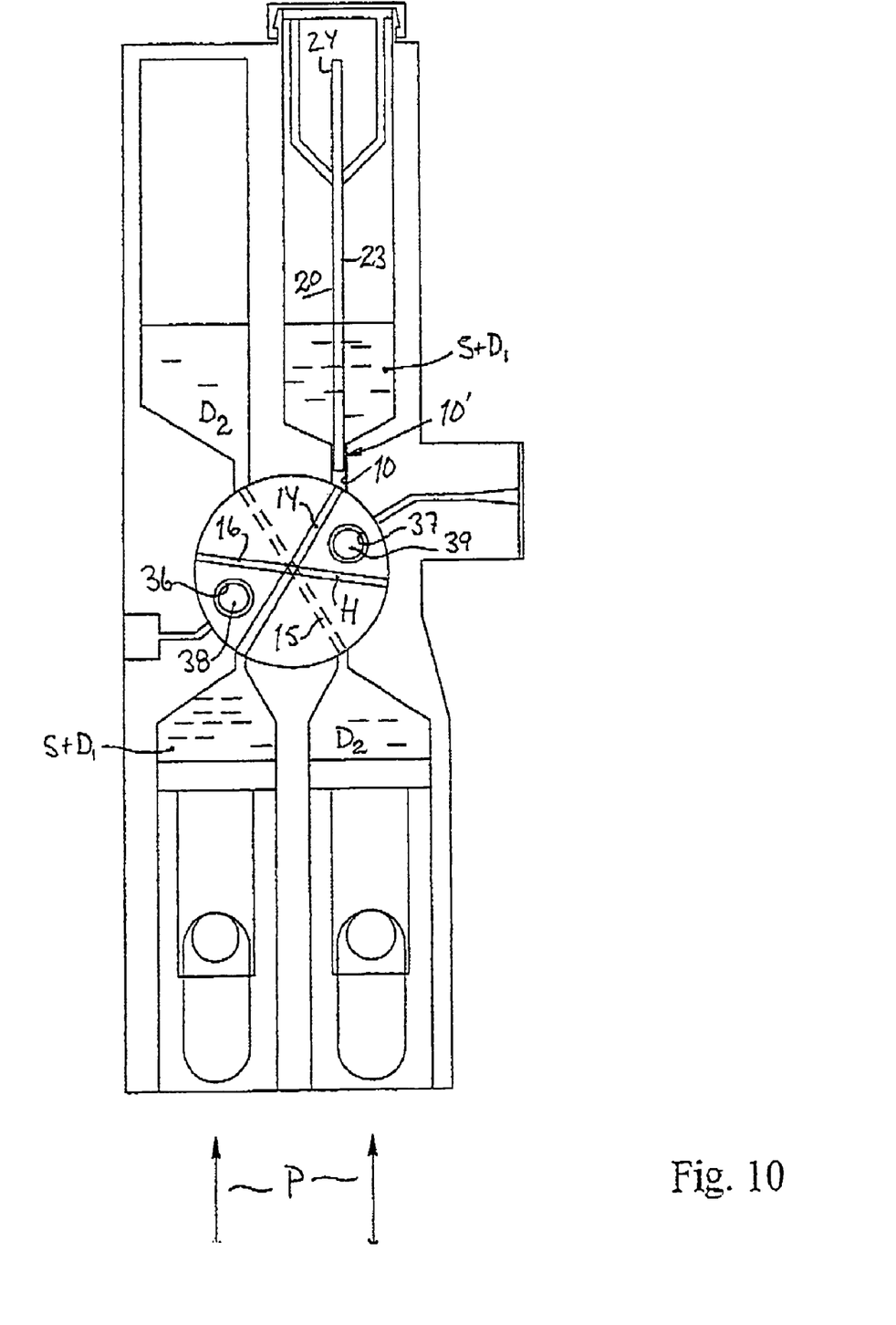
FIG. 10 is a front view of the apparatus shown in the valve position of FIGS. 5, 7 and 8 and with its plungers displaced to their extreme positive position.

FIG. 10 shows the situation during the first mixing operation when the pistons are reciprocating in the directions of arrows P to complete the mixing. The pistons are halted in an intermediate position shown in FIG. 11 leaving a major portion of the diluted sample (S+$D_1$) in the cylinder 27, and above all, a defined volume of first stage diluted sample in the channel 14.

Figure 11:
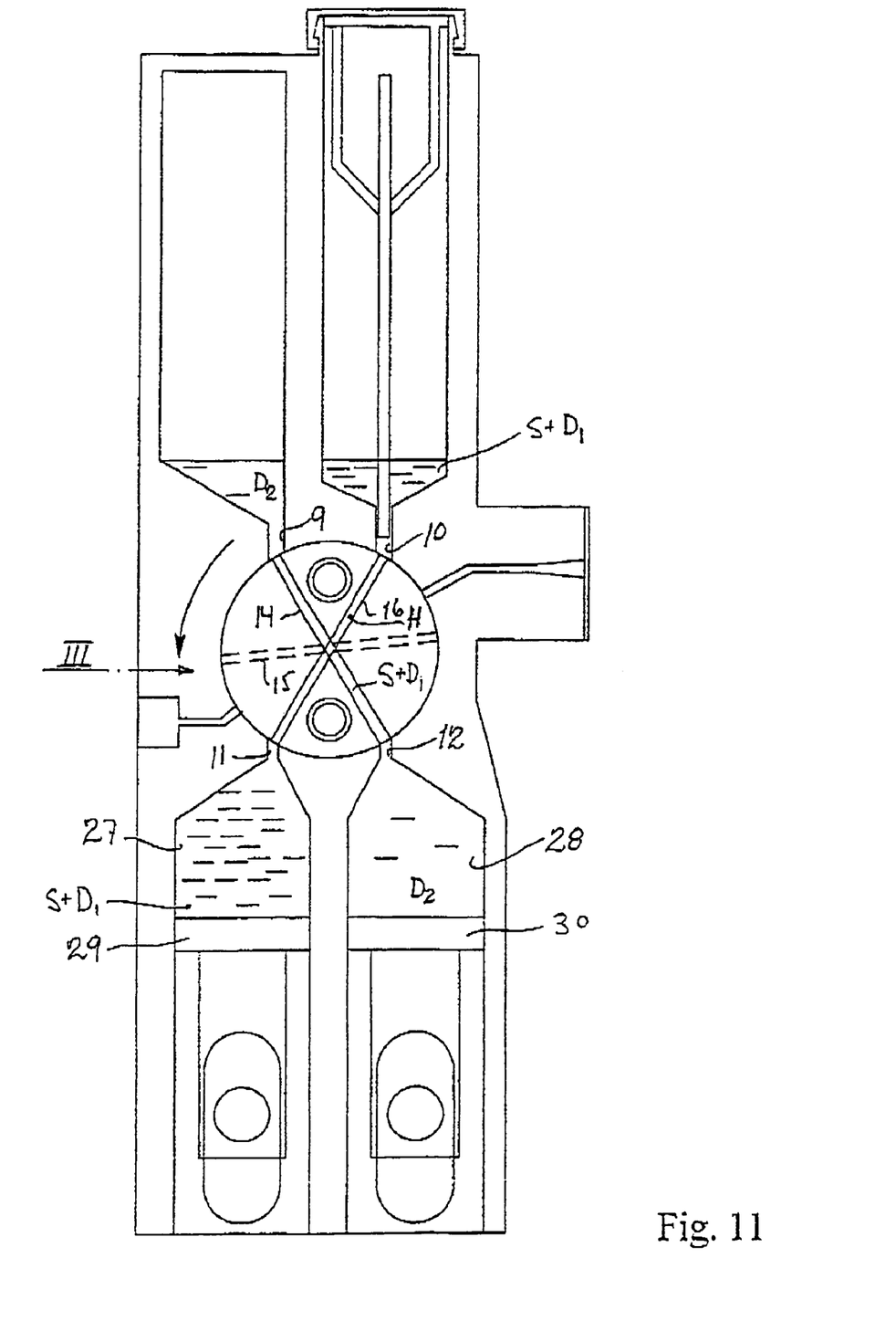
FIG. 11 is a front view of the apparatus having its plungers in an intermediate position and its valve rotated a further step to a third position.

In a following step, the turning valve is rotated counterclockwise to its third position III, where its channel 14 connects channels 9 and 12, and its channel 16 connects the channels 10 and 11 (FIG. 11). In this rotational position, channel 14 contains a defined volume of sample S and diluent $D_1$ (S+$D_1$), whereas channel 16 still contains its original contents of haemolysis agent H.

Figure 12:
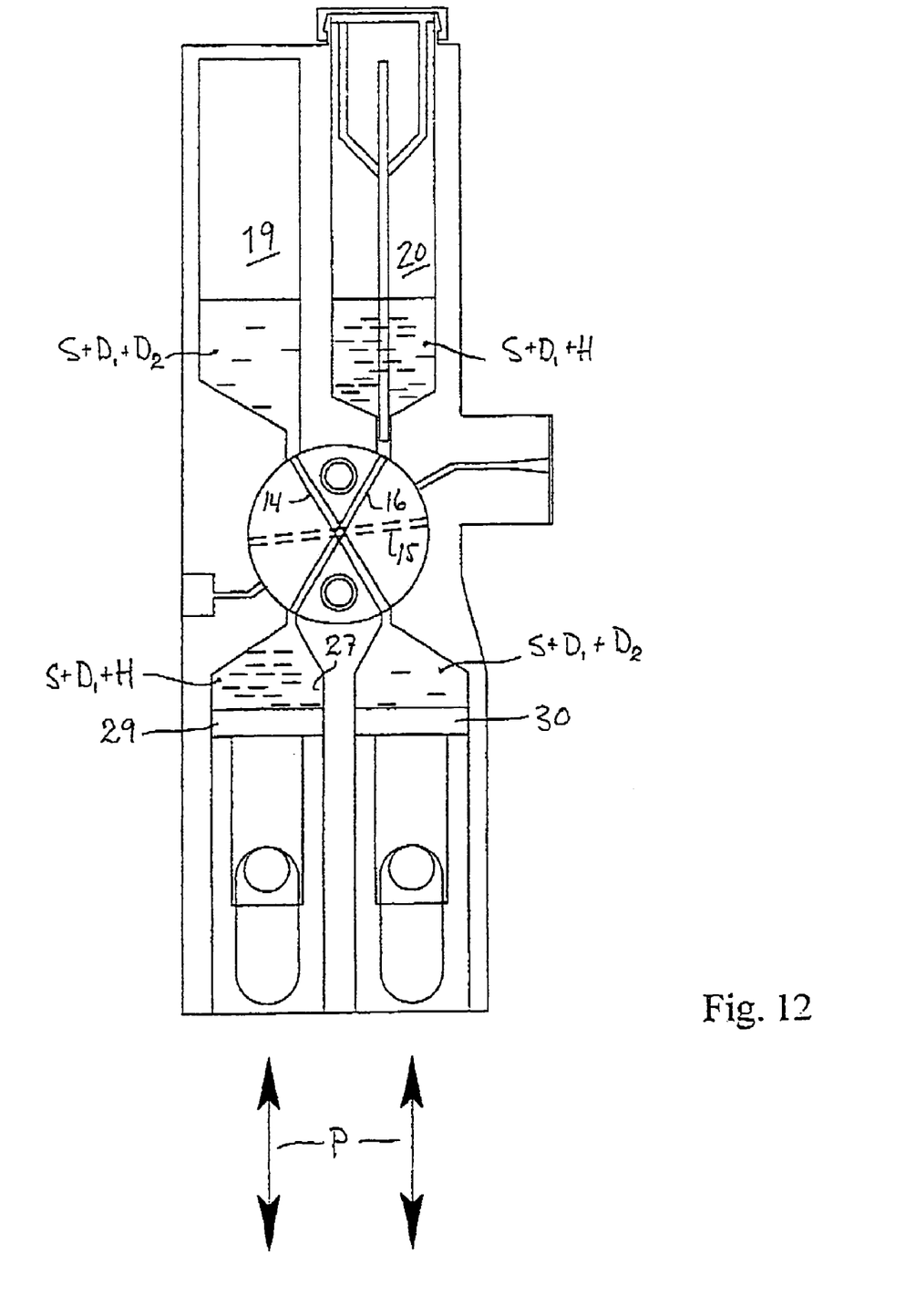
FIG. 12 is a front view of the apparatus having its valve in the third position and its plungers displaced to their extreme positive position.

Upward movement of the piston 29 as shown in FIG. 12, displaces the diluted sample (S+$D_1$) through the valve channel 16 to convey the haemolysis agent H therefrom into the recipient 20 to mix with the first stage mixture (S+$D_1$) to form a mixture (S+$D_1$+H). Simultaneous upward movement of piston 30 displaces the diluent $D_2$ from the cylinder 28 through the valve channel 14 containing a defined volume of first stage diluted sample S+$D_1$. This first stage sample, thus, will be mixed with the volume of diluent $D_2$ present in recipient 19 to provide a second stage diluted sample (S+$D_1$+$D_2$). Subsequent reciprocating movement of the pistons will complete the two simultaneous mixing processes, leaving a final dilution ratio of typically 1:200 in the cylinder 27 and the receptacle 20, and a final dilution ratio of typically 1:40000 in the cylinder 28 and the receptacle 19.

After this final dilution step, the measurements on the two differently diluted samples (S+$D_1$+H) and (S+$D_1$+$D_2$) are performed with the instrument mentioned. Apart from its operating arms, the instrument includes a measuring system having means for conducting at least parts of the contents in the receptacles 19 and 20 past measurement stations, where particle counting is performed, as well as means for controlling the volumes to be measured and means for flushing the various conduits of the measuring system. Such means are shown in FIGS. 8, 9, 13 and 14.

The measuring system includes two similar conduit branches 45*a*, 45*b*, one for each of the receptacles 19, 20. Each such branch starts with a needle portion 46*a*, 46*b* directed in parallel with the arms 38-41 so as to pierce corresponding diaphragms 47*a*, 47*b* sealing apertures 48*a*, 48*b* in the rear housing wall 7 communicating with the receptacles 19, 20, respectively. The needle portions are in fluid communication with conduits 49*a*, 49*b*. These are provided with cell counting stations 50*a*, 50*b*, each comprising a first electrode 51*a*, 51*b*, an orifice 52*a*, 52*b* and a second electrode 53*a*, 53*b*. The orifices are small apertures allowing statistically only one blood cell to pass at a time. By means of electric wires 54a, 55a and 54b, 55b, respectively, a voltage may be applied over the orifices, and any change in the resistance between the electrodes, indicating the passage of a blood cell to be counted, may be detected by suitable electronic equipment included in the instrument, and the sum of all resistance changes detected corresponds to the number of blood cells having passed through the orifice.

Each of the conduits 49a, 49b is branched into two sub-branch conduits 56a, 56b and 57a, 57b, respectively. The conduits 56a, 56b lead to a respective container 58a, 58b containing a flush liquid F. The flush liquid also fills the conduits 56a, 56b as well as the conduits 49a, 49b including the needle portions 47a, 47b. Valves 59a, 59b are mounted in the conduits 56a, 56b between the containers 58a, 58b and the sub-branch conduits 57a, 57b, respectively. Valves 60a, 60b are also mounted in the conduits 57a, 57b. The flush liquid F is filled into the conduits 56a, 56b to a level LF above the valves 60a, 60b.

Substantially vertical portions of the conduits 57a, 57b are provided with lower counting start detectors 61a, 61b and upper counting stop detectors 62a, 62b spaced defined distances.

Figure 13:
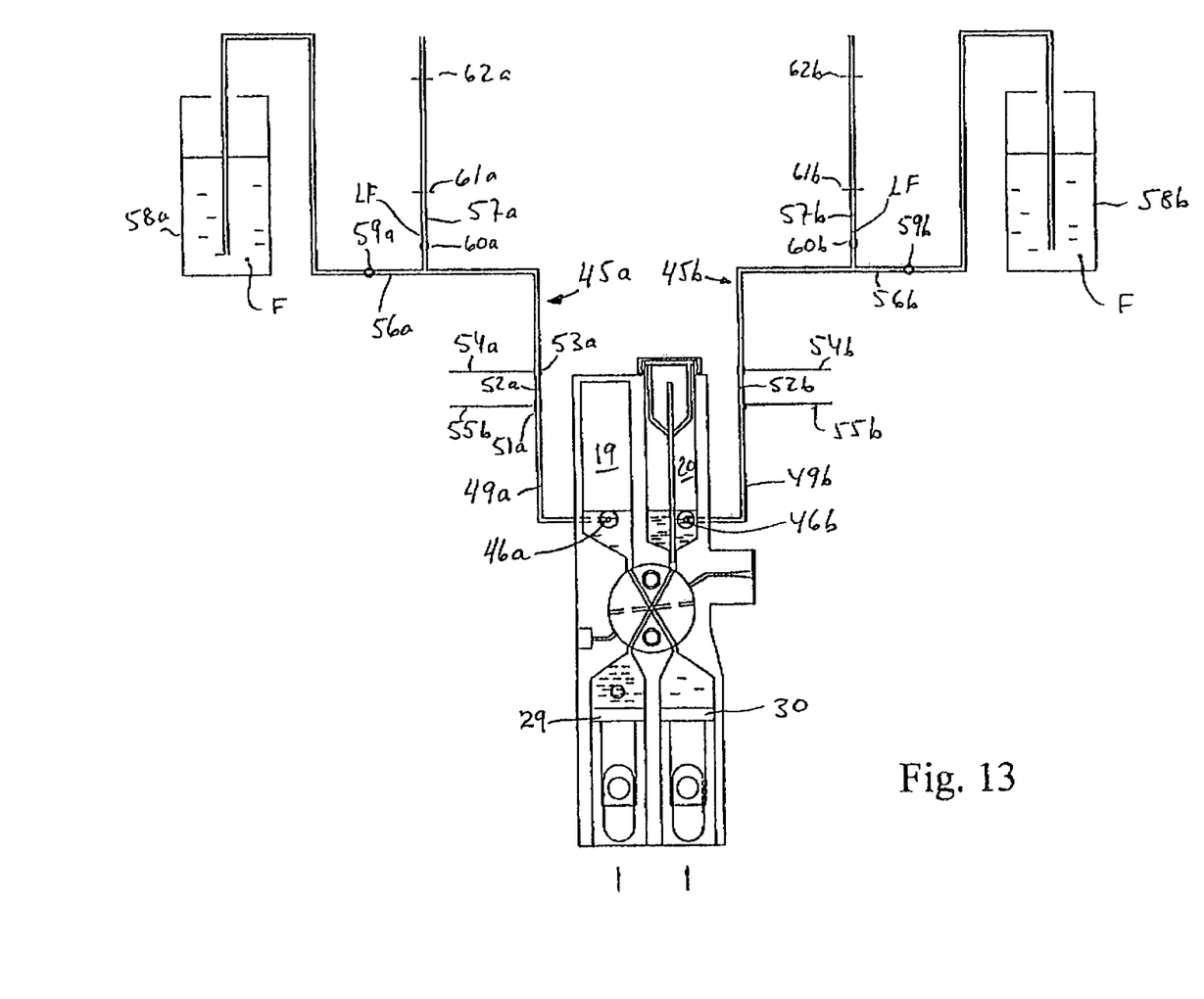
FIG. 13 is a view corresponding to that of FIG. 8, but showing the valve in its third position and its plungers moving towards their extreme positive positions.

After completing the simultaneous mixing operations described above with reference to FIG. 12, and before commencing the particle counting process, the valves 59a, 59b are closed, whereas the valves 60a, 60b are opened. Furthermore, the pistons 29, 30 must be brought to positions where the levels in the receptacles 19 and 20 are located above the needle portions 46a, 46b, as seen in FIG. 13.

From these positions, the pistons are further displaced upwards to press the respective contents of the receptacles 19, 20 through the needle portions 46a, 46b and into the conduits 49a, 49b. During this process, the flush liquid contained within the needle portions and the conduits will be displaced through the conduits 49a, 49b, including the electrodes 51a, 51b, the orifices 52a, 52b and the electrodes 53a, 53b, through the open valves 60a, 60b to raise the original level LF towards the respective lower detector 61a, 61b.

It should be emphasised at this stage of the description, that the various conduits shown in the drawings are not drawn in proper relative scales. In practice, and as will be evident for the skilled person, the volumes within the conduits 49a, 49b, including the needle portions 47a, 47b, up to the second electrodes 53a, 53b, are at least equal to the volumes within the conduits 57a, 57b between the valves 60a, 60b and the counting start detectors 61a, 61b.

In other words, the dimensioning of the conduits is such, that when the levels of the flush liquid in the vertical conduits 57a, 57b have reached the counting start detectors 61a, 61b, the respective diluted sample shall at least have reached its associated second electrode 53a, 53b, respectively.

Thus, when the level of the flush liquid has reached the respective counting start detector 61a, 61b, a signal is delivered to the instrument to start particle counting, i.e., to start recording each resistance change detected over the electrodes 51a, 53a and 51b, 53b, respectively. As soon as the levels LF in the conduits 57a, 57b have reached the respective upper detector 62a, 62b, a stop counting signal is delivered to the instrument and the corresponding results may be stored in the instrument and/or displayed on it.

During the counting process, the diluted blood samples never reach further along the conduits than to positions well before the respective branching point 49' of the conduits 49a, 49b.

After the counting process has been completed, the pistons 29, 30 are returned to positions where the levels LF in the conduits 57a, 57b are substantially as before starting the counting.

Figure 14:
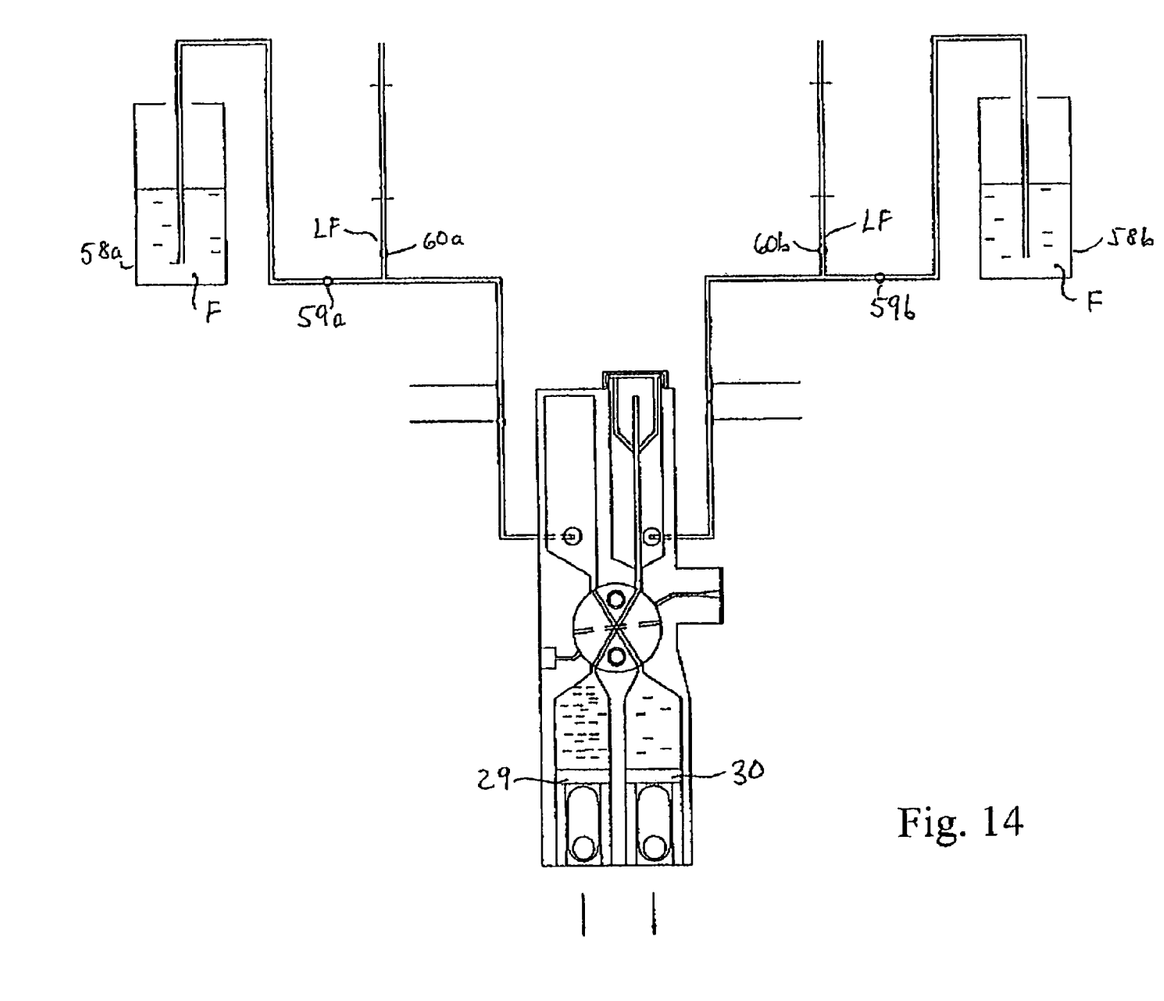
FIG. 14 is a view corresponding to that of FIG. 13, but showing the plungers in their extreme negative position after having performed a flush stroke.

At this stage, the valves 60a, 60b are closed, the valves 59a, 59b are opened, and the pistons 29, 30 are lowered to their bottom positions as shown in FIG. 14. During this process, flushing liquid F is withdrawn from the respective container 58a, 58b through the conduits 56a, 56b to completely flush through the conduits 49a, 49b, including the second electrodes 53a, 53b, the orifices 52a, 52b, the first electrodes 51a, 51b, and the needle portions 46a, 46b.

In this position, all possibly contaminated liquid is contained within the cylinders 27, 28. When finally removing the disposable apparatus housing 1 from the instrument, the elastic diaphragms 47a, 47b will effectively wipe off any diluted sample residue from the needle portions 46a, 46b.

The invention claimed is:

1. A disposable apparatus for use in blood testing and being adapted for simultaneous dilution of a blood sample into two different dilution ratios, said apparatus including a block-shaped housing having integrated therein:
   a first and a second receptacle, one of which, as a first blood sample receiver, being adapted to receive a blood sample;
   a first and a second container, each containing a defined volume of a diluent;
   a valve including a valve body having three valve body channels extending therethrough and being positionable in three distinct positions, one of which putting the receptacles in simultaneous communication with a respective one of the containers through pairs of the channels;
   displacers for displacing diluent and diluted sample through said valve body channels between said containers and said receptacles; and
   a third of said valve body channels containing a haemolysis agent, said third channel being connectable between a receptacle and its respective container in one of said three distinct positions of the valve.

2. The disposable apparatus according to claim 1, wherein said first blood sample receiver is adapted to receive a blood sampling capillary tube.

3. The disposable apparatus according to claim 1, wherein said valve is a turning valve.

4. A disposable apparatus for use in blood testing and being adapted for simultaneous dilution of a blood sample into two different dilution ratios, said apparatus including a block-shaped housing having integrated therein:
   a first and a second receptacle;
   a first and a second cylinder, each containing a defined volume of a diluent and each having a piston moveable therein for displacing diluent and diluted sample,
   a valve including a valve body having three valve body channels extending therethrough and being positionable in three distinct positions, one of which putting the receptacles in simultaneous communication with one each of the cylinders through pairs of the channels;
   one of the receptacles, as a first blood sample receiver, being adapted to receive a blood sampling capillary tube,
   wherein, in a second position of the valve body, a first of the valve body channels connects the second receptacle with the first cylinder, and a second of the valve body channels connects the first receptacle with the second cylinder.

5. The apparatus according to claim 4, wherein all said three valve body channels are out of communication with both said receptacles and both said cylinders in a first position of said valve body.

6. The apparatus according to claim 4, wherein a first housing channel opening in a first wall of the housing, as a second blood sample receiver, is adapted to receive a blood sample from a blood sampling cannula.

7. The apparatus according to claim 6, wherein an elastic diaphragm covers a mouth of said first housing channel, said diaphragm being pierceable by said cannula.

8. The apparatus according to claim 6, wherein, in the first position of the valve body, the first housing channel communicates with the first valve body channel and the first valve body channel communicates with a second housing channel opening in a wall of the housing opposite to said first wall.

9. The apparatus according to claim 4, wherein, in a third position of the valve body, the first valve body channel connects the first receptacle with the second cylinder and the third valve body channel connects the second receptacle with the first cylinder.

10. The apparatus according to claim 8, wherein, in a third position of the valve body, the first valve body channel connects the first receptacle with the second cylinder and the third valve body channel connects the second receptacle with the first cylinder.

11. The apparatus according to claim 4, wherein a third of said valve body channels contains a haemolysis agent.

12. The apparatus according to claim 4, wherein each of the receptacles has an aperture for transferring at least part of liquid contents in the receptacles to a respective measurement station.

13. The apparatus according to claim 12, wherein each aperture is covered by a pierceable diaphragm.

14. The apparatus according to claim 4, comprising a light path through at least one cylinder.

15. The apparatus according to claim 4, wherein the valve is a turning valve having a rotatable valve body.

16. An instrument for use with the apparatus according to claim 4, comprising operating members for the valve body and the pistons as well as conduits for fluid connection to the receptacles to direct fluid therefrom to measuring stations of the instrument.

17. The instrument according to claim 16, wherein the operating members and the conduits are simultaneously connectable to the valve body, the pistons and the apertures.

18. The disposable apparatus according to claim 1, wherein the haemolysis agent in said third valve body channel is in a dried state.

19. The disposable apparatus according to claim 1, wherein the haemolysis agent in said third valve body channel is in a fluid state.

20. A disposable apparatus for use in blood testing and being adapted for simultaneous dilution of a blood sample into two different dilution ratios, said apparatus including a block-shaped housing having integrated therein:
  a first and a second receptacle;
  a first and a second cylinder, each containing a defined volume of a diluent and each having a piston moveable therein for displacing diluent and diluted sample,
  a valve including a valve body having three valve body channels extending therethrough and being positionable in three distinct positions, one of which putting the receptacles in simultaneous communication with one each of the cylinders through pairs of the channels;
  one of the receptacles, as a first blood sample receiver, being adapted to receive a blood sampling capillary tube,
  wherein a third of said valve body channels contains a haemolysis agent.

* * * * *

UNITED STATES PATENT AND TRADEMARK OFFICE
CERTIFICATE OF CORRECTION

| | | |
|---|---|---|
| PATENT NO. | : 7,335,339 B2 | Page 1 of 1 |
| APPLICATION NO. | : 10/849239 | |
| DATED | : February 26, 2008 | |
| INVENTOR(S) | : Ingemar Berndtsson | |

It is certified that error appears in the above-identified patent and that said Letters Patent is hereby corrected as shown below:

Title page; please insert;

(30) <u>Foreign Application Priority Data</u>

<u>Nov. 21, 2001  [SE]   Sweden....................0103877-7</u>

Signed and Sealed this

Ninth Day of September, 2008

JON W. DUDAS
*Director of the United States Patent and Trademark Office*